United States Patent Office

Re. 28,093
Reissued July 30, 1974

28,093

WOUND-HEALING CARTILAGE POWDER

Leslie L. Balassa, Blooming Grove, N.Y., assignor to Lescarden Ltd., Goshen, N.Y.

No Drawing. Original No. 3,400,199, dated Sept. 3, 1968, Ser. No. 435,693, Feb. 26, 1965, which is a continuation-in-part of abandoned application Ser. No. 176,443, Feb. 28, 1962. Application for reissue Aug. 13, 1970, Ser. No. 63,669

Int. Cl. A61k *17/00*

U.S. Cl. 424—95 22 Claims

Matter enclosed in heavy brackets [ ] appears in the original patent but forms no part of this reissue specification; matter printed in italics indicates the additions made by reissue.

ABSTRACT OF THE DISCLOSURE

The invention pertains to wound-healing compositions comprising finely divided animal cartilage which is free of an interposition effect and which is characterized as having a substantially average maximum particle size of about 70 microns and an average particle size of between about 1 micron and about 40 microns. The invention also relates to methods of use of such material in a wound-healing method.

This application is a continuation-in-part of my copending application Ser. No. 176,443, filed Feb. 28, 1962, now abandoned.

This invention relates to wound-healing compositions and methods of making, improving and reactivating the same, and methods of treating and healing wounds.

It was observed some time ago that the healing of wounds of human patients is inhibited or retarded if the patients were at the same time undergoing cortisone treatment. It was found further that this inhibition of the healing of the wounds could be overcome in some instances by the use of cartilage powder applied locally.

It has also been shown that the healing of wounds has sometimes been accelerated by the use of rather coarse, hand-ground powder of acid-pepsin digested adult bovine tracheal cartilage having maximum particle size of about 400–450 microns. Experiments were carried out on albino Sherman strain female rats. There was observed a maximum average increase in the rate of healing and in the strength of the healed tissues of about 20%, over that of the control animals, the control animals being those with wounds untreated.

One of the problems involved in healing wounds has long been recognized as occurring in a primarily closed incision: when a composition is applied to such a wound, any excess in amount of such application at least initially produces a negative effect, which has sometimes been called the "interposition effect." This is the reduction in tensile strength observed when any substance is placed into a primarily closed wound, even in very small amounts. In the test data reported in this specification where the negative results are reported for prior art compositions such as gelatin, talc, collagen, etc., as well as when the compositions of this invention had been deactivated or degraded by one process or another, it appears that a major contributing factor to the negative results has been the "interposition effect." Thus, when the active composition of the invention demonstrates any improvement in the rate of wound healing, it should be remembered that the improvement has occurred in spite of the initial handicap of the "interposition effect" which must be overcome. Similarly, care must be exercised to avoid the use of excess quantities of the material of the present invention, to reduce the initial "interposition effect" in topical applications.

Investigation has been made of many compositions in the past, among them chondroitin sulfate, chondromucoprotein, carragheenan and collagen, and in every instance these have yielded no wound healing effect whatever. Most have given small negative results, probably as a result of the interposition effect. Other compounds tested including local hyaluronic acid, glucuronic acid, n-acetylglucosamine, and lysozyme were tested for wound-healing activity without significant effect. For example, parenteral injections on rats of the last three named substances were given on the first post-operative day. This time was chosen since it is on this day that injections of a saline extract of the cartilage of this invention have been shown to be effective. The local applications were at the same density as has been employed for such cartilage preparations (2–4 mg./cm.$^2$ of wound surface), while the parenteral injections were made from 5% solutions and were 2 cc. and 5 cc. in volume. All these tests were without any significant positive result.

I have now found that the particle size of the cartilage used has a surprisingly profound effect on the rate of healing and on the strength of the healed tissue. Not only is the rate of healing increased as the particle size of the cartilage is decreased, but also the manner or the process by which the cartilage is pulverized and the conditions prevailing during the pulverizing have a profound bearing on the results obtained with the cartilage powder. The effectiveness of the present invention has been demonstrated in comparative tests to be highly superior to results obtained on animals treated with either collagen, carragheenan, chondroitin sulfate, chondromucoprotein, fibrinogen, gelatin, talc, bone flour or systemic d-methionine. I have also found methods of further increasing the wound healing activity of the effective powders of this invention and methods of reactivating such powders after they have been inadvertently deactivated or otherwise reduced in activity.

Furthermore, I found most unexpectedly that cartilage taken from the partly calcified skeletons (including foetal skeletons) of very young or newly born animals is much more effective in accelerating the healing of wounds than was the case with the bovine tracheal cartilage powder on which previous observations were based, which included substantial quantities of coarse adult cartilage powder. Preferably the young animal is not over six months old.

While the present invention relates preferably to young cartilage, i.e., from young animals or young or newly regenerated cartilage from older animals as reptiles, whether finely divided or not, and cartilage from mature animals in finely divided (average particle size 40 microns or less) particle form, it is to be understood that the invention encompasses such cartilage in either the form which would in maturity retain the cartilaginous form or which would in maturity ossify to bone.

The cartilage may be prepared by any suitable means to result in a product which is essentially pure cartilage substance free from adhering tissue, which may have been removed by acid-pepsin or other suitable enzyme treatment, with or without mechanical assistance, or otherwise.

I have succeeded in preparing highly effective extracts by the use of aqueous solutions of materials which are in the pH range of about 6.5 to 10, and preferably between 5 and 8, at the concentrations employed in preparing the extracts. I prefer to use as extraction aids those which are either volatile and therefore can be readily removed from the extract by volatilization such as for example ammonia or ammonium carbonate, or such materials which if remaining in the extract would cause no harm if applied either topically or introduced parenterally. Dialysis may be employed to remove undesired salts or other dialyzable material which may be present. Other extraction aids are urea, sodium citrate, disodium phosphate, trisodium phosphate, sodium formate, sodium chloride, and similar compounds or mixtures of them.

I succeeded in concentrating the extracts and even obtained dry extracts of substantially unimpaired activity and which could be redissolved or diluted back to the original strength with saline solution by concentrating the extracts in vacuum at low temperature or by freeze-drying them. Subjecting the cartilage or the cartilage powder or the extracts of the invention to irradiation by ultra violet light for a short period of time may increase the activity of the material to a noticeable degree. Irradiation with ionizing radiation such as gamma rays may also increase the activity of the cartilage.

I have found a surprising synergistic effect in the combination of cartilage powder or cartilage extract of the invention with growth hormone. This effect can be observed both in topical and in parenteral applications.

I succeeded in obtaining satisfactory effects through oral administration of suitably pelletized or encapsulated cartilage powder or cartilage extracts of the invention.

The present invention provides dosage units of effective wound healing quantity of cartilage powder from a young animal, or from a mature animal, having average particle size between about 1 micron and about 40 microns, or a substantial maximum particle size of about 70 microns, incorporated into a clinically acceptable wound healing carrier vehicle such as unguent, oil, salve, solution, extract, powder, etc. The invention also contemplates methods of enhancing the wound healing activity of a cartridge powder and of restoring wound healing activity in substantially inactivated cartilage powder including partially deactivated cartilage powder. Novel methods are also provided whereby finely divided cartilage powder may be stabilized before, during or after the final comminution stage of production thereof. Various techniques for the extraction of active wound healing components, agents, and compositions from cartilage powder are included within the present invention.

I found that there were very great differences in the activity of the preparations, depending on the method used in their preparation, the auxiliaries or carrier employed, and in the technique of application. For example, the cartilage powder as well as the extract were effective when they were absorbed or incorporated with surgical gauze which then was applied to the wound and when the same materials were applied by spraying onto the wound. Also clinically acceptable carrier vehicles for the effective cartilage powder or extract, such as salves based on aqueous gels such as those from alginates, gum tragacanth, gelatin, gluten, casein, polyvinylpyrrolidone, dextran and many others are effective in many applications. They are also convenient to apply especially over large areas such as is the case with burns.

The effective cartilage powder or cartilage extracts suspended in oils such as tung oil, corn oil, olive oil, or linseed oil, may be applied directly to wounds. The oil dispersions may be emulsified in water, forming oil-in-water type emulsions, or conversely, water may be emulsified in the oil dispersions forming water-in-oil type emulsions. The cartilage and cartilage extracts dispersed in aqueous or oil carriers may be applied directly to the wounds by spraying, brushing, by impregnating in bandaging materials or by any other means which makes it possible to bring the cartilage or its extract into intimate contact with the tissues. In the case of parenteral applications the cartilage or cartilage extract preparations may be introduced subcutaneously, intra-muscularly, intravenously, or through suppositories introduced into rectal or other cavities. Cartilage powders dispersed in suitable oils have been successfully administered orally. Cartilage powder may be administered, as orally, in the form of pellets such as tablets or capsules. On the other hand, by incorporating the cartilage powder onto silica gel or other gel forming materials which are capable of coating the stomach walls, the rate of healing of stomach ulcers may be noticeably increased.

The invention has been used with humans in treatment of keloids (hardened scar tissue). The keloid was initially cut out and resutured in the presence of the calf cartilage powder of the invention. After more than six months periodic observation, the keloid did not reappear and apparently the invention prevented the re-formation of the keloid scar tissue, contrary to the usual experience of frequent recurrence of keloid formation.

The cartilage saline extract of this invention has also demonstrated a market anti-inflammatory effect. For example, as when introduced parenterally in the areas affected by psoriasis, almost immedaite reduction of the inflammation was observed.

The statistical average of scores of tests involving the application of the cartilage of the present invention shows that there were produced increases of over 50% in the tensile strengths of seven-day old midline abdominal wounds in rats. The increase in wound healing rate was even further enhanced when a combination of optimal size (between about 10 and about 30 microns average diameter) and optimal age of the cartilage source (calf) were combined, in an average of which cases maximal increase in wound tensile strength substantially higher than 50% was achieved. Wound strength increase averaging 50% results in less likelihood of wound disaster, less likelihood of wound infection, the capability of removing sutures earlier with attendant further lessening or likelihood of infection as well as further acceleration in final wound healing rate, thereby resulting in earlier discharge of the patient from care and safer post-care experience.

Furthermore, as the cartilage treated wound ages in accordance with the present invention, it does not become a mass of essentially acellular collagen as does the cicatrix of the untreated wound. Instead, it continues to proliferate in humans activity up to 40 days after wound and frequently longer. It does not however, become hypertrophic or keloidal, and, in fact, appears less bulky than the corresponding control wounds. These observations point to the presence of inhibitory activity in the cartilage of the invention, in addition to the accelerator factor.

The local use of the finely ground calf cartilage powder is of great clinical value in the treatment of nongranulating wounds of 50 different kinds, without untoward effects, either locally or systemically, as demonstrated in application to the primarily closed wounds of 87 human surgical incisions in a wide variety of procedures. There was no immediate or late evidence of antigenicity.

Controlled tensiometric observations in 15 human volunteers utilizing in each instance paired incisions in the same individual with tensiometry from 7 to 14 days after wounding have shown that the wound treated therein locally with the cartilage preparation of the present invention has been so much stronger than the untreated wounds as to exhibit a measured mean positive differential of approximately 50% over the control value.

The cartilage preparations of the present invention have been successfully utilized to accelerate and to improve the healing of the following types of wound, either by topical application or by injection of saline extract: chemical burns, third degree skin burns, radioactive injury, chest wall, abdominal and other wounds, operative and post-operative wounds, penetrating wounds such as those of thorax and abdomen, ulcers due to arteriosclerosis and to trophic disturbance, ulcers of skin, gangrene of skin due to the trauma or physical agent or to undetermined cause, dermatitis, lupus erythemathosus with ulcer, keloids, atopic eczema, parapsoriasis and psoriasis. Other types of wounds also have responded successfully to the cartilage preparations of this invention with improved results. For example, the invention is especially useful in cases involving cortisone or other steroid treatment (known to retard healing) or involving diabetes.

Test methods.—Unless otherwise stated, the effectiveness of the preparations of the examples herein was established in animal tests as described by J. Prudden, G. Nishihara and L. Baker in "The Acceleration of Wound Healing with Cartilage-I," Surgery, Gynecology & Obstetrics 105: 283 (1957).

Sherman strain albino female rats were employed in the tests. The preparation consisted of 5.5 centimeter midline abdominal incision under controlled conditions and closed with interrupted through-and-through sutures of No. 000 silk.

The wound tensile strength at seven days is determined in millimeters of mercury by a modification of the technique of the method illustrated in the publication cited above.

The rat to be tested is killed by an intracardiac injection of paraldehyde or by exposure to toxic fumes such as to diethyl ether. The test is made prior to the onset of rigor mortis. After the sutures have been removed from the wound, a rubber latex prophylactic pouch is inserted into the peritoneal cavity through a defect made with a Kelly clamp in the apex of the vagina. After the rubber pouch is in place, and the introitus has been snugged firmly (with a hermostat) around the tube leading to the peritoneal cavity, the rotary air pump connected to the pouch is turned on regulating it in such a manner that the air pressure will increase at a rate of 10 millimeters of mercury every five seconds. The pressure at which the wound splits and the pouch extrudes itself (wholly or in part) through the defect is recorded as the tensile strength of the wound. This is also a quantitative measure of the degree of healing or rate of healing achieved in the experiments.

The following examples illustrate certain present preferred embodiments of the invention, and it is understood that other methods and embodiments within the spirit of the invention may be made without departing from the scope of the appended claims. Parts and ratios are by weight except as otherwise stated.

EXAMPLE 1.—CARTILAGE PEBBLE MILL-GROUND

The tracheas of healthy adult beef cattle were removed within 30 to 60 minutes after the animals were slaughtered. The traceas were then either processed immediately with an acid-pepsin solution or they were frozen to preserve them, in which case the acid-pepsin digestion may be deferred. The tracheas either fresh or previously frozen were then digested for about six hours at 50° C. in an aqueous solution containing 0.6% acetic acid (U.S.P. glacial) and 0.3% pepsin (N.F. IX grade, 3500 activity). After digestion the tracheal cartilage was removed from the acid-pepsin solution, washed first with water of about 70° C. and then with water of about 25° C. until the effluent wash water showed no trace of pepsin or acetic acid. The cartilage was dried in vacuum (20 mm. mercury) at 80° C. The dried cartilage was defatted by extracting it with a solvent, such as hexane. It was then granulated.

The granulated purified cartilage was ground to a fine powder in a laboratory four-quart size porcelain jar mill, loaded with one-inch size (average) flint pebbles in a weight ratio of 1 cartilage to 2 pebbles. Dry Ice ($CO_2$) was then put on top of the mill charge and the mill was kept open for 5 minutes to allow the $CO_2$ to displace the air in the mill. The lid of the mill was then clamped on tight and the mill rotated as is customary in the performance of the grinding operation. The grinding was carried out at about −20° C. for 96 hours. The ground cartilage was screened through a 325 mesh nylon screen, thereby confining the active cartilage powder to particles less than about 40 microns in size, and having average or majority particle size between about 5 and 10 microns.

EXAMPLES 1–A, 1–B AND 1–C

In these examples the same procedure was followed as described in Example 1 in the preparation of the cartilage powder of the invention, except that grinding times differed to obtain different grinds, and the cartilage source in Example 1–C was great white shark jaw cartilage which was ground in a mechanical mortar. The test method described above was performed to compare the rate of wound healing of each Example 1–A, 1–B and 1–C with control wounds which were untreated. The percent of wound healing stated was 100% for the control and represented increases as stated below for the examples of the invention, each figure representing the average of about 20 to over 40 controlled pairs of tests:

| Example | Cartilage used | [Maximum] *Particle* size *(average)* | Rate of healing (percent) |
|---|---|---|---|
| Control | None | | 100 |
| 1–A | Calf tracheal | Approx 70μ | 130 |
| 1–B | do | Approx. 20μ | 152.5 |
| 1–C | Grezt white shark jaw | Approx. 70μ | 130 |

EXAMPLE 2.—CARTILAGE PEBBLE MILL-GROUND

Cartilage obtained from the skeleton of a two-day old piglet was washed with distilled water immediately after removal from the carcass. The cartilage was then freed from the adhering tissue matter and then digested with an acid-pepsin solution [was] *as* described in Example 1. The cartilage was ground and screened in accordance with the method described in Example 1.

EXAMPLE 3.—BOVINE TRACHEAL CARTILAGE FLUID ENERGY MILL-GROUND

The freshly extracted bovine tracheal cartilage was washed with distilled water, and then digested with an acid-pepsin solution in accordance with the procedure described in Example 1.

The granulated cartilage was put through a fluid energy mill of the "Micronizer" type having an 8-inch diameter grinding chamber operated with nitrogen at 100 p.s.i.g. pressure, 100 c.f.m. (ft.$^3$/min.) volume, 20° C. temperature and at a solid feed rate of 10 lbs./hour.

The average particle size of the ground material taken from the collector attached to the mill was 5 microns with 10 microns as the maximum.

EXAMPLE 4

Cartilage from a variety of sources was ground in a fluid energy mill under the conditions indicated as follows:

| Cartilage source | Grinding fluid | Tmpera-ture)° C.) | Particle size, microns | |
|---|---|---|---|---|
| | | | Average | Maximum |
| b Bovine tracheal | Steam | 240 | 3 | 5 |
| c do | Air | 25 | 5 | 8 |
| d do | Air | −10 | 5 | 10 |
| e do | Oxygen | 25 | 5 | 7 |
| f do | Nitrogen | 25 | 5 | 7 |
| g do | do | −10 | 5 | 7 |
| h do | Argon | 25 | 5 | 7 |
| i Piglet, 1 day old | Nitrogen | 25 | 5 | 8 |
| j Piglet, 2 weeks old | do | 25 | 5 | 8 |
| k Piglet, 1 month old | do | 25 | 5 | 8 |
| l Piglet, 6 months old | do | 25 | 5 | 8 |
| m Calf, 1 day old | do | 25 | 5 | 8 |
| n Calf, 2 weeks old | do | 25 | 5 | 8 |
| o Calf, 1 month old | do | 25 | 5 | 8 |
| p Dog, 1 day old | do | 25 | 5 | 8 |
| q Dog, 2 weeks old | do | 25 | 5 | 8 |

EXAMPLE 5.—PREPARATION OF CARTILAGE EXTRACTS IN THE PEBBLE MILL

Extracts of cartilage having high wound-healing activity were produced as follows:

The cartilage was acid-pepsin digested as in Example 1, granulated, and then without drying was suspended in the extracting liquid and then transferred into a pebble mill which was charged to 50% of its volume with flint pebbles of average size, one inch diameter. The ratio of the cartilage to extracting liquid was kept to 25:75. The liquid suspension was charged into the mill in a quantity just sufficient to fill the voids of the pebbles with the top of the pebbles barely covered by the liquid. The air was then purged from the mill with nitrogen and the mill closed. The mill was allowed to run for 6 hours at between 3° C. and 4° C. which resulted in a medium fine grinding of the cartilage and in the simutlaneous extraction of the active wound-healing agent from the cartilage.

At the end of the 6-hour cycle, the mill was emptied, the fluid paste strained free of the pebbles, the fluid transferred into a centrifuge operated at 6000 r.p.m. and at a temperature of between 3° C. and 4° C. After one-half hour the centrifuge was stopped and the supernatant liquid strained through a 400 mesh nylon screen. If the stained extract was cloudy, it was returned to the centrifuge and the centrifuging repeated until a clear slightly opalescent extract was obtained.

The extracts were stored at 4° C. preserved with 1:10,000 sodium ethyl mercuric thiosalicylate.

The following extracts were thus prepared:

EXAMPLE 5

| Cartilage source | Extracting liquid | Total solids of clear extract by weight percent |
|---|---|---|
| a Bovine tracheal | Distilled water | 1.3 |
| b do | Isotonic saline sol | 5.2 |
| c do | Ammonia (25%) 1% in water | 6.5 |
| d do | 2% urea in water | 9.6 |
| e do | 1% ammonium carbonate in water. | 6.4 |
| f do | 1% disodium phosphate in water. | 6.6 |
| g do | 3% ammonium carbonate in water. | 7.2 |
| h do | 1% trisodium phosphate in water. | 7.6 |
| i do | 1% sodium citrate in water | 7.0 |
| j do | 3% sodium citrate in water | 9.2 |
| k do | 1% sodium formate in water | 8.2 |
| l Piglet 1 day old | Isotonic saline solution | 6.4 |
| m do | 1% ammonia (28%) in water | 7.1 |
| n do | 3% ammonium carbonate in water. | 8.1 |
| o do | 3% sodium citrate in water | 10.0 |
| p Calf one day old | Isotonic saline solution | 6.2 |
| q do | 1% ammonia (28%) in water | 7.3 |
| r do | Isotonic saline solution plus ammonia to pH 8. | 8.2 |

NOTE.—The isotonic saline solution was prepared with distilled water and contained 0.9% NaCl.

In addition to pebble mill and fluid energy mill grinding, satisfactory powders may be obtained by ball milling, hammer milling in inert atmosphere. While ball or pebble milling the cartilage with the extracting liquid gives satisfactory results, other methods, such as mixing the cartilage powders in the liquids with a high speed, high shear, closed turbine mixer or passing the extraction mixture through a pressure homogenizer, preferably at pressures in excess of 4000 p.s.i. will also give extracts of high activity.

EXAMPLE 6.—SPRAY-DRYING OF CARTILAGE EXTRACTS

Dry concentrates were prepared from cartilage extracts as follows:

A laboratory "Bowen" type spray dryer was used with the following modifications. In place of the oil furnace, electric heating coils were used to supply the heat energy necessary for the evaporation of the volatile portions of the extracts. Instead of air, nitrogen was used for the hot gas. A vaned disc, rotating at about 20,000 r.p.m. was used to atomize the extracts. The inlet gas temperature was held to about 280° F., the outlet temperature was between 140° F. and 160° F. The dryer was used as a closed system dryer with the exclusion of oxygen to avoid degrading the active material during the evaporation of the water.

The following dry extracts were thus produced:

| | Extract used | Solids, percent | Yield, percent | Appearance of dried powder |
|---|---|---|---|---|
| a | Example 5-b | 5.2 | 4.8 | Sl. yellow. |
| b | Example 5-c | 6.5 | 6.2 | Do. |
| c | Example 5-h | 7.6 | 7.3 | Do. |
| d | Example 5-j | 9.2 | 8.9 | Off white. |
| e | Example 5-l | 6.4 | 6.2 | Sl. yellow. |
| f | Example 5-m | 7.1 | 6.8 | Do. |
| g | Example 5-o | 10.0 | 9.8 | Off white. |
| h | Example 5-p | 6.2 | 6.0 | Sl. yellow. |
| i | Example 5-q | 7.3 | 7.1 | Do. |
| j | Example 5-r | 8.2 | 8.0 | Do. |

The "solids percent" means percent of solids in the extracting liquid as determined by drying at 100° C. for two hours.

"Yield percent" means the dry solids percent obtained from the liquid by the drying process.

The spray-dried powders were stored in tightly closed glass jars in a refrigerator at 4° C.

EXAMPLE 7.—FREEZE-DRYING OF CARTILAGE EXTRACTS

A laboratory vacuum shelf dryer was used. The extracts were refrigerated to −10° C. The shelf temperature was 50° C. The vapor pressure was about 0.8 mm. Hg. The "solids percent" was determined at 100° C.

| | Extract used | Solids, percent | Yield, percent | Appearance of dried material |
|---|---|---|---|---|
| a | Example 5-b | 5.2 | 5.1 | Off white coarse powder |
| b | Example 5-c | 6.5 | 6.5 | Do. |
| c | Example 5-h | 7.6 | 7.8 | Do. |
| d | Example 5-j | 9.2 | 10.1 | Do. |
| e | Example 5-l | 6.4 | 6.5 | Do. |
| f | Example 5-m | 7.1 | 7.3 | Do. |
| g | Example 5-o | 10.0 | 10.8 | Do. |
| h | Example 5-p | 6.2 | 6.3 | Do. |
| i | Example 5-q | 7.2 | 7.6 | Do. |
| j | Example 5-r | 8.2 | 8.5 | Do. |

The freeze-dried materials were stored in tightly closed glass jars in a refrigerator at 4° C.

EXAMPLE 8

Cartilage powders are applied to wounds by dusting with a hand atomizer about 30 mg. into a 5.75 cm. longitudinal midline abdominal incision of the female rat. Of the 30 mg. applied to the wounds about 10–15 mg. was effectively utilized at the sites of the wound. It is preferred that the dosage unit be applied to the wound in an amount substantially equivalent to between about 10–15 mg. per square centimeter.

| Cartilage powder: | Rate of wound healing (percent) |
|---|---|
| 1. None, control | 100 |
| 2. Example 1 | 125 |
| 3. Example 2 | 135 |
| 4. Example 3 | 130 |
| 5. Example 4–b | 100 |
| 6. Example 4–c | 110 |
| 7. Example 4–d | 120 |
| 8. Example 4–e | 105 |
| 9. Example 4–f | 130 |
| 10. Example 4–g | 135 |
| 11. Example 4–h | 130 |
| 12. Example 4–i | 140 |
| 13. Example 4–j | 140 |
| 14. Example 4–k | 135 |
| 15. Example 4–l | 130 |
| 16. Example 4–m | 140 |
| 17. Example 4–n | 140 |
| 18. Example 4–o | 135 |
| 19. Example 4–p | 142 |
| 20. Example 4–q | 135 |

"Rate of wound healing" related to 100 means the ratio, expressed as percent, of pressure required to rupture the healed tissue of the wound as compared with the pressure required for rupture of the wound of the untreated control animal, according to the test method described above.

EXAMPLE 9

Cartilage extracts applied to wounds by swabbing to 5.75 cm. longitudinal midline abdominal incision of the female rat.

| Cartilage extract (liquid): | Rate of wound healing (percent) |
|---|---|
| 1. None, isotonic saline-control | 100 |
| 2. Example 5–a | 100 |
| 3. Example 5–b | 125 |
| 4. Example 5–c | 125 |
| 5. Example 5–d | 125 |
| 6. Example 5–e | 125 |
| 7. Example 5–f | 130 |
| 8. Example 5–g | 115 |
| 9. Example 5–h | 130 |
| 10. Example 5–i | 130 |
| 11. Example 5–j | 130 |
| 12. Example 5–k | 135 |
| 13. Example 5–l | 140 |
| 14. Example 5–m | 140 |
| 15. Example 5–n | 130 |
| 16. Example 5–o | 135 |
| 17. Example 5–p | 140 |
| 18. Example 5–q | 145 |
| 19. Example 5–r | 150 |

EXAMPLE 10

The effect of parenterally injected cartilage extracts on the healing of wounds. In each case 5 cc. of the extract was injected into the subcutaneous tissue on the rat's back within 24 hours after the abdominal incision.

| Cartilage extract (liquid): | Rate of wound healing (percent) |
|---|---|
| 1. None, isotonic saline-control | 100 |
| 2. Example 5–a | 105 |
| 3. Example 5–b | 120 |
| 4. Example 5–f | 125 |
| 5. Example 5–i | 130 |
| 6. Example 5–l | 135 |
| 7. Example 5–p | 135 |
| 8. Example 5–r | 140 |

EXAMPLE 11

This example demonstrates the effect of parenterally injected cartilage extracts combined with a bovine growth hormone. In each case 5 cc. of the extract was mixed with 10 mgm. of a bovine growth hormone, distributed by the Endocrinology Study Section of the National Institutes of Health through the pituitary hormone distribution program. Approximate assay of the growth hormone:

| | |
|---|---|
| Adenocorticotrophic hormone | 0.06 U.S.P. milliunit/mgm. |
| Porlactin | 0.1 International unit/mgm. |
| Vasopressin | 0.01 U.S.P. unit/mgm. |
| Thyreotrophic hormone | 0.008 U.S.P. unit/mgm. |
| Oxytocin | 0.008 U.S.P. unit/mgm. |

Test animals and wounds are as stated in Example 10.

| Cartilage extract (liquid): | Rate of wound healing (percent) |
|---|---|
| 1. None, isotonic saline-control | 100 |
| 2. None, isotonic saline with growth hormone control | 108 |
| 3. Example 5–a with growth hormone | 110 |
| 4. Example 5–b with growth hormone | 110 |
| 5. Example 5–f with growth hormone | 135 |
| 6. Example 5–i with growth hormone | 135 |
| 7. Example 5–l with growth hormone | 145 |
| 8. Example 5–p with growth hormone | 145 |
| 9. Example 5–r with growth hormone | 148 |

EXAMPLE 12

This example demonstrates the value of reconstituted spray-dried and freeze-dried extracts in the healing of wounds. The dried extracts were dissolved either in water or in isotonic saline solution, depending on the salt content of the original preparation. The solutions were adjusted to correspond with the solids content of the extracts from which the dried materials were prepared. The solutions were applied by parenteral injections into rats in Example 10.

| Dried Extract | Solvent | Rate of wound Healing (percent) |
|---|---|---|
| 1. None | Isotonic saline-control | 100 |
| 2. Example 6–a | Water | 115 |
| 3. Example 7–a | do | 120 |
| 4. Example 6–b | Isotonic saline | 125 |
| 5. Example 7–b | do | 130 |
| 6. Example 6–e | Water | 130 |
| 7. Example 7–e | do | 135 |
| 8. Example 6–h | do | 140 |
| 9. Example 7–h | do | 145 |
| 10. Example 6–i | do | 140 |
| 11. Example 7–i | do | 145 |

EXAMPLE 13

This example demonstrates the value of intravenous injections of cartilage extracts or solutions of dried extracts in the healing of wounds. These were made on dogs with circular incisions. Wounds were not saturated but protected only with sterile dressing. The rate of healing was measured by observing the degree of granulation as compared with the control.

| Extract: | Rate of wound healing (percent) |
|---|---|
| 1. None, isotonic saline-control | 100 |
| 2. Example 5-b | 120 |
| 3. Example 5-l | 135 |
| 4. Example 5-p | 135 |
| 5. Example 5-r | 140 |
| 6. Examples 12-10 | 140 |
| 7. Examples 12-11 | 145 |

EXAMPLE 14

This example demonstrates the use of cartilage powder on open wounds. Powders were held between layers of porous fabric, i.e., surgical gauze, and held through bandages to the unsutured wound. Tests were made on dogs. The rate of healing was estimated by observing the degree of granulation.

| Cartilage powder: | Rate of wound healing (percent) |
|---|---|
| 1. None, dry gauze-control | 100 |
| 2. Example 2 | 135 |
| 3. Example 4-f | 135 |
| 4. Example 4-i | 145 |
| 5. Example 4-m | 145 |

EXAMPLE 15

This example demonstrates the effect of applying liquid cartilage extracts on open wounds. Porous fabric i.e., surgical gauze was saturated with the extracts and applied to the open an unsutured wounds while still wet. Tests were made on dogs. The rate of healing was measured by the observed degree of granulation.

| Cartilage extract: | Rate of wound healing (percent) |
|---|---|
| 1. None, isotonic saline-control | 100 |
| 2. Example 5-b | 125 |
| 3. Example 5-l | 140 |
| 4. Example 5-p | 140 |
| 5. Example 5-r | 150 |

EXAMPLE 16

This example demonstrates the effect of applying dried cartilage extract on open wounds. Porous fabric, i.e., surgical gauze, was saturated with the extracts, dried to a moisture content of about 5% at 30° C. and at a pressure of 50 mm. mercury. The dried gauze was applied to the open and unsutured wounds. Tests and observations were as in Example 15.

| Cartilage extract: | Rate of wound healing (percent) |
|---|---|
| 1. None, isotonic saline-control | 100 |
| 2. Example 5-b | 120 |
| 3. Example 5-l | 135 |
| 4. Example 5-p | 135 |
| 5. Example 5-r | 150 |

EXAMPLE 17

These tests involved the intravenous injection of cartilage extracts combined with one or more blood extenders, such as whole blood, blood plasma, and a plasma substitute, namely polyvinylpyrrolidone or dextran. Tests were made on dogs. In carrying out these tests 100 cc. blood was taken from the animal and treated as follows:

I. The blood was mixed with 10 cc. cartilage extract and reinjected into the same animal.

II. The plasma was obtained from the blood mixed with 10 cc. cartilage extract and reinjected into the same animal from which the blood was obtained.

III. The blood was replaced by an equal volume of an isotonic aqueous saline solution of polyvinylpyrrolidone 3.5%, viscosity grade K-30 and 10 cc. of a cartilage extract.

The control animals were treated as follows:

Control 1—100 cc. blood taken and then reinjected into the same animal;

Control 2—The blood taken as in case of Control 1, the plasma separated and reinjected into the same animal;

Control 3—The blood was taken from the animal as above in case of Control 1, and replaced with a saline solution of 3.5% polyvinylpyrrolidone viscosity type K-30.

Note: All blood samples taken were citrated to prevent coagulation. The rate of healing was measured by the observed degree of granulation.

| | Cartilage extract | Test as per— | Rate of healing (percent) |
|---|---|---|---|
| 1 | None, Control 1 | | 100 |
| 2 | None, Control 2 | | 90 |
| 3 | None, Control 3 | | 85 |
| 4 | Example 5-b | I | 130 |
| 5 | do | II | 125 |
| 6 | do | III | 120 |
| 7 | Example 5-l | I | 150 |
| 8 | do | II | 145 |
| 9 | do | III | 130 |
| 10 | Example 5-p | I | 150 |
| 11 | do | II | 145 |
| 12 | do | III | 135 |

The animals used in these experiments weighed not less than 30 lbs. each.

EXAMPLE 18.—CARTILAGE SUPPOSITORIES

Suppositories were prepared with 20% cartilage powder and 80% suppository base. The suppository base was prepared in accordance with U.S.P. XVI, pages 828-9, Glycerinated Gelatin Suppositories. The suppositories were 2 gm. size and were administered rectally to dogs. The surface of the rectum was removed for 1 cm. from the rectal opening, about one hour before the insertion of the suppository. A fresh suppository was introduced every six hours. The rate of healing was determined by visual observation.

| Cartilage powder: | Rate of wound healing (percent) |
|---|---|
| 1. None, control | 100 |
| 2. None, suppository base-control | 105 |
| 3. Example 4-f | 130 |
| 4. Example 4-m | 135 |

EXAMPLE 19

Cartilage powder tablets and capsules were orally administered. The tablets were prepared without and with enteric coatings. The capsules were either gelatin or enteric material such as carboxymethyl cellulose. Both the tablets and the capsules contained 2 gm. cartilage powder each. The test animals were dogs and the wounds were circular unsutured. The dosage was 0.1 gm. cartilage powder/1-lb. body weight every six hours. The rate of healing was determined by visual observation.

| | Cartilage powder | Form | Coating | Rate of wound healing (percent) |
|---|---|---|---|---|
| 1 | None, control) | | | 100 |
| 2 | Example 4-f | Tablet | None | 115 |
| 3 | do | do | Enteric | 120 |
| 4 | do | do | Gelatin | 115 |
| 5 | do | Capsule | do | 115 |
| 6 | Example 4-m | do | do | 125 |
| 7 | do | do | Enteric | 130 |

EXAMPLE 20.—IRRADIATED CARTILAGE POWDER

Cartilage powder was irradiated with ultra violet radiation produced by a high pressure quartz mercury arc tube "Hanovia" type LL. The thickness of the powder layer exposed to radiation was 5 mm., the radiant source was 15 cm. from the cartilage powder. The exposure time was one minute. The experiment was carried out in a nitrogen atmosphere. The irradiated powders were tested on rats as in case of Example 8.

| Cartilage powder: | Rate of wound healing (percent) |
|---|---|
| 1. None, control | 100 |
| 2. Example 4–f not irradiated, control | 130 |
| 3. Example 4–f | 135 |
| 4. Example 4–m | 150 |

EXAMPLE 21.—STERILIZATION WITH AN ANTISEPTIC ALCOHOL, 70%

Mix the calf cartilage powder of the invention with an excess of about 70% (volume) ethyl alcohol. A sufficient excess of alcohol is present when the cartilage powder forms a mobile slurry with the powder. The particle size of the powder controls the volume of alcohol required to form the mobile slurry. The smaller the particle size the larger the volume of alcohol is required.

In general, 2 ml. alcohol mixed with each gram of a 30 micron average particle size cartilage powder is well in excess of the minimum required to form the slurry.

The alcohol slurry of the cartilage powder is best mixed at a rate to keep the powder suspended in the liquid. The cartilage swells somewhat and becomes gummy under the influence of the 70% alcohol.

In about 30 minutes the cartilage is sterilized by the alcohol. However, this sterilized cartilage, due to its swollen condition and gummy character, is difficult to filter and forms a hard crust when dried. This hard crust has then to be reground to the original particle size.

The difficulties caused by the swelling and gummy nature of the sterilized cartilage can be overcome by centrifuging the slurry to form a firm cartilage sediment, decanting the supernatant liquid and replacing it with anhydrous alcohol.

The cartilage sediment, mixed with the anhydrous alcohol, is dehydrated regaining substantially its original particle size and losing its gumminess. This dehydrated cartilage can be readily filtered and dries to a free flowing powder.

EXAMPLE 22.—STERILIZATION WITH ISOPROPYL ALCOHOL

Anhydrous isopropyl alcohol sterilizes the cartilage as well as 70% ethyl alcohol and in about the same time, i.e., about 30 minutes, without swelling the cartilage particles or causing gumminess.

The cartilage slurry prepared with isopropyl alcohol can be readily filtered and the filter cake so obtained can be dried to a free flowing powder.

The sterilization either with ethyl alcohol or with isopropyl alcohol can be carried out satisfactorily at ambient room temperatures, although sterilization at elevated temperautres may reduce the time required.

EXAMPLE 23.—STERILIZATION OF THE CARTILAGE POWDER BY HEAT

Cartilage powder of the invention, surprisingly, is sterilized, without loss of wound healing activity, by heating it to about 125–132° C. for 3–4 hours, substantially in the absence of air or oxygen. Other temperatures, as low as 110° C., may be utilized, but for longer periods of time to achieve sterilization.

The preferred procedure is to place the cartilage powder in a vessel with some Dry Ice over it and then covering the vessel loosely with a metal foil. The vessel is placed in a vacuum oven, the oven is connected with a vacuum pump and the air is evacuated to a vacuum of about 10 mm. of mercury. The oven is then heated to about 127° C. and held there for about four hours. It is important that the entire mass of material in the vessel be heated through and maintained at about 125 to 132° C. for about three to four hours.

The heat sterilized powder is ready for clinical use.

EXAMPLE 24.—REACTIVATION AND ENHANCEMENT OF CARTILAGE BY HEAT IN THE ABSENCE OF OXYGEN

This example illustrates lowering of the activity of calf cartilage powder when milled in the presence of air, and air together with heat, respectively, followed by the restoration and further enhancement of the wound healing activity when the partially or totally inactivated material is exposed to heat of about 127° C. for between 5 hours to 50 hours and in the virtual absence of air or oxygen (Tests 6 and 8).

The cartilage powder was inactivated by hammer milling it under conditions of excessive aeration and some generation of heat (Test 5).

The activity of the cartilage was lowered to about one-third of its activity by ball milling it in the presence of air (Test 7), as compared with the same material ball milled in a $CO_2$ atmosphere (Test 4).

The heating of the cartilage was done in the following manner: a vacuum oven (Freas, size No. 504, Fisher Scientific Co.) was loaded with the cartilage powder and with a small quantity of Dry Ice (solid $CO_2$). About 15 to 25 grams of the Dry Ice were placed in an open dish in the oven. The door of the oven was closed, the air evacuated to about 10 mm. pressure, the vacuum pump was disconnected, and the heating cycle started. During heating there was some pressure build-up in the oven caused by the expansion of the Dry Ice as it becomes gaseous carbon dioxide.

| Test: | Rate of wound healing (percent) |
|---|---|
| 1. Control, no cartilage | 100.0 |
| 2. Calf cartilage, lot 1AX, ball milled in $CO_2$ | 127.7 |
| 3. #2, heated in $CO_2$, 4 hrs., 45 min., 130° C. | 130.5 |
| 4. Calf cartilage, lot 2AX, ball milled in $CO_2$ | 137.2 |
| 5. #4, hammer milled in air with heat generation | 100.0 |
| 6. #5, heated in $CO_2$ for 42 hrs., 128° C. | 136.7 |
| 7. Calf cartilage, lot 2AX, ball milled in air | 110.9 |
| 8. #7, heated in $CO_2$ for 5½ hrs. 127° C. | 129.1 |

The above test results were based on 20 to over 40 pairs of animals (Sherman strain albino rats) for each of the eight tests enumerated above and the percent figure represents the statistical average of all such tests.

Comparison of Test 3 with Test 2 shows that heat sterilization of the powder of this invention may be accomplished together with enhancement (130.5 vs. 127.7%) of wound healing rate.

Comparison of Test 5 with Test 4 shows that highly effective powder of this invention may be completely deactivated by hammer-milling air with heat generation.

Comparison of Test 6 with Test 5 shows that the thus deactivated hammer-milled powder may be reactivated by prolonged heating as stated.

Comparison of Test 7 with Test 4 shows that ball milling highly effective powder of the invention in air seriously lowers (from 137.2 to 110.9%) the rate of wound healing.

Comparison of Test 8 with Test 7 shows that heating of the degraded powder of Test 7 in $CO_2$ at elevated temperature reactivates the material to a highly effective rate of wound healing.

EXAMPLE 25

Forty wounds involving a wide spectrum of human chronic nonhealing types of ulcers were treated according to the present invention.

The types of wounds treated were as follows:

| | No. of wounds |
|---|---|
| 1. Chronic varicose ulcer on bedrest or after surgical correction of venous incompetency | 16 |
| 2. Chronic nonhealing ulcers of the abdomen following wound disruption in cachectic patients with inoperable carcinoma | 6 |
| 3. Radiation ulcer | 1 |
| 4. Ulcers of the extremities in chronic ulcerative colitis (gangrenous pyoderma) | 2 |
| 5. Nonhealing perineal defects in individuals having undergone total colectomy for chronic ulcerative colitis (not on steroids) | 10 |
| 6. Nonhealing chest wall defect following necrosis of flaps in radical mastectomy | 1 |
| 7. Ulcers of the extremities in patient with systemic lupus erythematosus on massive steroid therapy | 4 |

There was no particular sex or age distribution except that all were adults and none was older than 60 or younger than 25.

In each instance the local therapy was:

At the time of the dressing, the wound was thoroughly cleansed with hydrogen peroxide, and washed with alcohol. It was dried with gauze. The cartilage preparation was applied by atomizing the powder onto the surface and into the wound. In 38 of the 40 cases this treatment resulted in the transformation of the wound surface from a nongranulating, sluggish, dirty grey surface to a typical pink, healthy granulating bed within ten days. In the other two cases a somewhat longer time was required.

EXAMPLE 26

The cartilage powder of the invention was atomized into 83 surgical wounds in 39 human patients with 47 operations, as follows:

CARTILAGE POWDER INSTILLATION IN CLOSED SURGICAL WOUNDS

| Type of operation | No. operations | No. wounds |
|---|---|---|
| (1) Bilateral phlebectomies | 7 | 43 |
| (2) Cholecystectomy (with and without common duct drainage); right subcostal incision | 5 | 5 |
| (3) Gastrectomy, linea alba incision | 1 | 1 |
| (4) Exploratory laparotomy for regional enteritis with emaciation and partial mechanical obstruction, midline incision | 1 | 1 |
| (5) Hysterectomy; midline incision | 1 | 1 |
| (6) Breast biopsy (circum-areolar) | 1 | 1 |
| (7) Inguinal herniorrhaphy | 22 | 22 |
| (8) Cecotomy for excision villous adenoma (right lower abdominal oblique) | 1 | 1 |
| (9) Lipomectomy | 1 | 1 |
| (10) Pilonidal cystectomy | 1 | 1 |
| (11) Small bowel resection for obstructing mesenteric tumor metastic from pancreas (midline incision) | 1 | 1 |
| (12) Abdominoperineal resection for squamous cell carcinoma of anus (midline incision) | 1 | 1 |
| (13) Ventral herniorrhaphy | 1 | 1 |
| (14) Anterior resection of rectosigmoid (midline incision) | 1 | 1 |
| (15) Resection terminal 30 in. of ileum proximal to ileostomy for regional ileitis; (reopening midline incision used for previous total colectomy) | 1 | 1 |
| (16) Lysis of adhesions and vagectomy (midline) | 1 | 1 |
| Total | 47 | 83 |

In all 83 cases there was primary healing of all wounds except for intermediate suture abscess formation which was followed by healing without event. In none of these cases was there any abnormal liver chemistry, disturbed renal function, or evidence of sensitivity to the material of the invention. In no case was the wound nonflexible, thick or keloidal and all wounds appeared to be more flexible and less bulky than normally expected.

EXAMPLE 27

Calf tracheal cartilage powder having maximum particle size of 40 microns was mixed with about an equal part of anhydrous propylene glycol. This premix was then added to "Neobase" (an ointment base made by Burroughs Wellcome & Co. of Tuckahoe, N.Y.), which contains the following ingredients:

Glyceryl monostearate
Tween-61 (polyoxyethylene sorbitan monostearate)
Span-60 (sorbitan monostearate)
Paroleine (liquid paraffin)
Propylene glycol
Methyl-p-hydroxybenzoate
Water (about 50% or more)

diluted with about 50% additional water in an amount to yield a composition having about 10% of said powder.

Thus, a useful wound healing or dermatological salve was formed, although it is to be understood that other ointments and salves and salve bases may incorporate the powder or extract of the present invention.

EXAMPLE 28

An ointment particularly useful with surgical gauze was formulated by mixing the following:

| | Parts by weight | |
|---|---|---|
| | Ex. 29-A | Ex. 29-B |
| Polyethylene glycol, mol. wt. 4,000 | 5 | 5 |
| Polyethylene glycol, mol. wt. 1,540 | 30 | 25 |
| Polyethylene glycol, mol. wt. 300 | 60 | 60 |
| Cartilage powder, maximum particle size 40μ | 50 | 10 |

This ointment is useful in certain dermatological applications and the physical properties may be further adjusted and controlled by varying the ratios of the polyethylene glycols or adding required amounts of propylene glycol and/or glycerol.

While isotonic saline is an effective extraction medium, more complete extraction with higher healing activity is obtained when the pH is raised slightly with ammonia. Salts other than NaCl provide more effective extraction, as shown in Example 5. An inert atmosphere during the extraction results in extracts of greater potency than when the extraction is carried out in the presence of oxygen. Since the presence of oxygen during processing has completely inactivated extracts of the cartilages herein shown otherwise to be vastly superior, the use of suitable known nontoxic antioxidants such as ascorbic acid or its salts or vitamin A may permit carrying out the extraction in the presence of some air without serious loss of potency.

Though bovine tracheal cartilage from mature animals, i.e., a year old or older, is for some purposes a satisfactory source, cartilage with substantially greater potency is obtained from the skeletons of very young animals. The highest potency material is generally obtained from animals less than one month old, although cartilage from adolescent animals taken before maturity may be used in this invention without excessively fine grinding. Young animals are intended to mean those which are still adolescent and have not yet reached maturity. Cartilage from foetal skeletons is often effective. Finely divided cartilage from other mammals, in addition to bovine and porcine and canine, is effective in healing wounds in accordance with the present invention: for example, finely divided cartilage powder from rat trachea and the human knee have been successfully utilized in accordance with the invention; so also with other animals such as the finely divided cartilage of birds, fish, jaw-bone of shark, rib cage of a crocodile (South American caiman known to be one year old, as obtained from the New York City Zoological Gardens, in early adsolescence). Finely divided reptile cartilage is particularly effective in view of the extraordinary ability of the reptiles to regenerate their tissues and even their limbs. For example, young cartilage from the tail of a tegu salamander, which tail had regenerated for three months, obtained from the same zoo was used without excessively fine grinding in effective wound healing experiments. Cartilage from the rib cage of young lambs taken prior to ossification was successfully utilized.

When dry cartilage extract is desired, freeze-drying is preferred, but spray-drying is satisfactory in inert atmosphere. Vacuum drying is satisfactory when oxygen is excluded and temperature of the liquid is held below 40° C.

The cartilage powder may be dusted on the wound or atomized on it. It may also be applied in the form of ointment on the wound, as exemplified above. The extract may also be applied directly to the wound by spraying it on the wound, swabbing it on, or brushing it on. Both the powder and the extract may be applied first to an absorbent medium which is then applied to the wound and held on by a bandage or adhesive tape, or other suitable means. The cartilage or the extract may be incorporated into tablets, capsules or suppositories and applied orally, rectally or in the vaginal or uteral passages. Implantation as pellets and injection of solution of the extract of the invention has been effective.

Cartilage extracts may be injected subcutaneously, intramuscularly or intravenously. The dried extracts may be used as powders or they may be reconstituted and used as the original extracts. The wounds to which the active materials are applied may be sutured or may be left open without materially affecting the rate of healing. The active materials may be administered once, preferably within the first 24 hours of the incision; or they may be applied before the incision or they may be applied in several applications in succession. Irradiating the cartilage powder with ultraviolet radiation in the absence of oxygen increases its activity.

While certain present preferred embodiments of the invention *have* [has] been described and exemplified herein, it is to be understood that the invention may be otherwise embodied within the spirit thereof and within the scope of the appended claims.

What is claimed is:

1. A dosage unit comprising an effective wound healing quantity of a non-interposing cartilage powder having a substantial maximum particle size of about 70 microns, and an average particle size between about 1 micron and about 40 microns from a young cartilage-containing animal.

2. A dosage unit comprising an effective wound healing quantity of a non-interposing cartilage powder having a substantial maximum particle size of about 70 microns, and an average particle size between about 1 micron and about 40 microns from a young cartilage-containing mammal.

3. A non-interposing cartilage powder having a substantial maximum particle size of about 70 microns, and an average particle size between about 1 micron and about 40 microns in dosage unit form from a young cartilage-containing vertebrate.

4. The composition of claim 1 having average particle size of about 5 to 10 microns.

5. A dosage unit comprising an effective wound healing quantity of a non-interposing cartilage powder having a substantial maximum particle size of about 70 microns and an average particle size between about 1 micron and about 40 microns from a young cartilage-containing animal incorporated into a clinically acceptable wound healing carrier vehicle.

6. A non-interposing cartilage powder in dosage unit form from a cartilage-containing animal and having a substantial maximum particle size of about 70 microns, and an average particle size between about 1 micron and about 40 microns.

7. The sterilized product of claim 6.

8. A non-interposing cartilage powder from a cartilage-containing animal having an average particle size between about 1 micron and about 40 microns and having a substantial maximum particle size of about 70 microns.

9. The irradiated cartilage powder of claim 8.

10. The process of treating a wound in an animal which comprises applying thereto the composition of claim 1

11. The process of treating a wound in an animal which comprises applying thereto the composition of claim 6.

12. A dosage unit according to claim 1, comprising an effective wound-healing quantity of a noninterposing cartilage powder having a substantial maximum particle size of about 70 microns and an average particle size between about 1 micron and about 40 microns derived from shark or reptilian cartilage.

13. A dosage unit according to claim 12, wherein the cartilage powder is derived from shark cartilage.

*14. A method of healing a wound of psoriasis in a human consisting essentially of the step of parenterally injecting into said human systemically or in the areas affected by psoriasis, an effective wound healing dose of an aqueous solution consisting essentially of at least the aqueous soluble portion of defatted, and essentially pure cartilage ground to a powder, free from adhering tissue, said cartilage being derived from a cartilage-containing animal.*

*15. A method of healing a wound according to claim 14 wherein said wound is characterized by inflammation which is reduced upon treatment with said aqueous solution.*

*16. A method of healing a wound according to claim 15 wherein said effective wound healing dose is administered in a saline solution.*

*17. A method of healing a wound according to claim 14 wherein said cartilage-containing animal is a young animal.*

*18. A method of healing a wound of dermatitis in an animal which consists essentially of the step of topically applying or parenterally injecting into said wound an effective dose for healing dermatitis of an aqueous solution consisting essentially of at least the aqueous soluble portion of defatted, and essentially pure cartilage ground to a powder, free from adhering tissue, said cartilage being derived from a cartilage-containing animal.*

*19. A method of healing an ulcer wound requiring healing in an animal which comprises parenterally injecting into the area affected by said wound in said animal, an effective wound healing dose of an aqueous solution consisting essentially of at least the aqueous soluble portion of defatted, and essentially pure cartilage ground to a powder, free from adhering tissue, said cartilage being derived from a cartilage-containing animal.*

*20. A method of healing a burn wound in an animal which comprises parenterally injecting into the area affected by said burn wound in said animal an effective wound healing dose of an aqueous solution consisting essentially of at least the aqueous soluble portion of defatted, and essentially pure cartilage ground to a powder, free from adhering tissue, said cartilage being derived from a cartilage-containing animal.*

*21. The dosage unit of claim 5 wherein said clinically acceptable wound healing carrier vehicle is a suppository.*

*22. The dosage unit of claim 5 wherein said clinically acceptable wound healing carrier vehicle is an ointment.*

References Cited

The following references, cited by the Examiner, are of record in the patented file of this patent or the original patent.

UNITED STATES PATENTS

| | | | |
|---|---|---|---|
| 3,318,774 | 5/1967 | Dingwall et al. | 424—95 |
| 3,400,199 | 9/1968 | Balassa | 424—95 |
| 3,476,855 | 11/1969 | Balassa | 424—95 |
| 3,478,146 | 11/1969 | Balassa | 424—95 |

(Other references on following page)

OTHER REFERENCES

Lattes et al., Amer. J. Pathology *32* (5): 979—991, September-October 1956.

Prudden et al., Surg. Gyn. Obs. *105*: 283–286, September 1957.

Prudden, Transplantation Bulletin *5* (1): Jan. 14, 1958, p. 14.

Anderson et al., J. Bone & Joint Surgery *41*A (8): 1455–1468, December 1959.

Schwartz et al., Surgical Forum *10*: 308–311 (1960).

Jasinski et al. Path. Microbiol *24*: 148–153 (1961).

Paulette et al., Surg. Gyn. Obst. 108: 406–408, April 1959.

Inoue, Arch. Surg. *82*: 432–434, March 1961.

Anderson et al. J. Bone & Joint Surg. 43A: 980–1004, October 1961.

SHEP K. ROSE, Primary Examiner